(12) United States Patent
Xiao et al.

(10) Patent No.: US 11,369,317 B2
(45) Date of Patent: Jun. 28, 2022

(54) METHOD AND APPARATUS FOR CORRECTING INTERFERENCE IN RESPIRATORY NAVIGATION, AND STORAGE MEDIUM

(71) Applicant: Siemens Healthcare GmbH, Erlangen (DE)

(72) Inventors: Nan Xiao, Shenzhen (CN); De He Weng, Shenzhen (CN); Yan Tu Huang, Shenzhen (CN); Qiong Zhang, Shenzhen (CN)

(73) Assignee: Siemens Healthcare GmbH, Erlangen (DE)

( * ) Notice: Subject to any disclaimer, the term of this patent is extended or adjusted under 35 U.S.C. 154(b) by 25 days.

(21) Appl. No.: 16/858,264

(22) Filed: Apr. 24, 2020

(65) Prior Publication Data
US 2020/0337643 A1 Oct. 29, 2020

(30) Foreign Application Priority Data
Apr. 26, 2019 (CN) .......................... 201910345083.0

(51) Int. Cl.
*A61B 5/00* (2006.01)
*G01R 33/565* (2006.01)
*A61B 5/055* (2006.01)
*A61B 5/08* (2006.01)

(52) U.S. Cl.
CPC .............. *A61B 5/721* (2013.01); *A61B 5/055* (2013.01); *G01R 33/56509* (2013.01); *A61B 5/08* (2013.01)

(58) Field of Classification Search
CPC .... G01R 33/56509; A61B 5/055; A61B 5/721
See application file for complete search history.

(56) References Cited

U.S. PATENT DOCUMENTS

| | | | | |
|---|---|---|---|---|
| 7,683,620 B2 * | 3/2010 | Lin | ...................... | G01R 33/485 |
| | | | | 324/309 |
| 8,489,174 B2 * | 7/2013 | Stemmer | ............ | G01R 33/5676 |
| | | | | 600/410 |
| 9,396,561 B2 * | 7/2016 | Dumoulin | ............. | G06T 11/003 |
| 10,444,310 B2 * | 10/2019 | Poole | ..................... | G01R 33/38 |

(Continued)

OTHER PUBLICATIONS

Speier et al., "PT-Nav: A Novel Respiratory Navigation Method for Continuous Acquisition Based on Modulation of a Pilot Tone in the MR-Receiver," ESMRMB 129:97-98, 2015 // DOI: 10.1007/s10334-015-0487-2.

*Primary Examiner* — Dixomara Vargas
(74) *Attorney, Agent, or Firm* — Banner & Witcoff Ltd.

(57) ABSTRACT

In a method for correcting the interference in respiratory navigation, transmitting, during magnetic resonance scanning, a respiratory signal generated by a radio frequency signal generator to a human body; acquiring, as a measured respiratory signal, a respiratory signal passing through the human body and acquired in a local coil, wherein the measured respiratory signal is constituted by a real respiratory signal and an interference signal; determining, according to a respiratory signal coil sensitivity of the real respiratory signal and an interference signal coil sensitivity of the interference signal, a signal relation that is satisfied by the real respiratory signal, the interference signal and the measured respiratory signal; and calculating the signal relation to obtain the real respiratory signal.

18 Claims, 5 Drawing Sheets

(56) References Cited

U.S. PATENT DOCUMENTS

| | | | |
|---|---|---|---|
| 10,539,637 B2* | 1/2020 | Poole | G01R 33/383 |
| 2008/0272782 A1* | 11/2008 | Lin | G01R 33/5616 |
| | | | 324/312 |
| 2011/0152668 A1* | 6/2011 | Stemmer | G01R 33/5676 |
| | | | 600/413 |
| 2013/0343625 A1* | 12/2013 | Samsonov | G01R 33/5611 |
| | | | 382/131 |
| 2015/0369896 A1* | 12/2015 | Dagher | G01R 33/4806 |
| | | | 324/309 |
| 2016/0071291 A1* | 3/2016 | Samsonov | G01R 33/5611 |
| | | | 600/410 |
| 2017/0367672 A1* | 12/2017 | Samsonov | A61B 6/032 |
| 2018/0177428 A1* | 6/2018 | Peacock, III | G01R 33/34069 |
| 2018/0321347 A1* | 11/2018 | Wang | A61B 5/055 |
| 2019/0056470 A1* | 2/2019 | Wang | G01R 33/5601 |
| 2019/0104940 A1* | 4/2019 | Zhou | A61B 5/0073 |

* cited by examiner

METHOD AND APPARATUS FOR CORRECTING INTERFERENCE IN RESPIRATORY NAVIGATION, AND STORAGE MEDIUM

CROSS REFERENCE TO RELATED APPLICATIONS

This patent application claims priority to Chinese Patent Application No. 201910345083.0, filed Apr. 26, 2019, which is incorporated herein by reference in its entirety.

BACKGROUND

Field

The present disclosure relates to the field of magnetic resonance imaging. Particularly, the present disclosure relates to a method and apparatus for correcting the interference in respiratory navigation, and a storage medium.

Related Art

In many cases of existing magnetic resonance (MR for short) imaging, there is a problem that imaging quality is affected by artifacts generated due to the respiratory motion of a patient. In this case, it is necessary to track the respiratory motion through respiratory navigation so as to compensate for the respiratory motion during magnetic resonance imaging, thereby eliminating the artifacts. In the prior art, there is a pilot tone navigator (PT-Nav for short) technique in which respiratory motion is tracked based on receiving a pilot signal modulated by a human body in a magnetic resonance receiver without additional scanning of integrated hardware or interruption of a stable state, thereby reducing costs.

However, when MR local coils are used as signal receivers, an inherent problem thereof arises: strong interference occurs to the pilot signal when an MR imaging pulse sequence is run. Therefore, when the pilot signal is used to track the respiratory motion, for example, in curves of signals in different channels shown in FIG. 1 and a curve of signals obtained after integrating signals in all channels shown in FIG. 2, received signals are very different from "real" respiratory signals in that the respiratory curves have severe distortion with many "signal drops," which causes a severe degradation of the quality of obtained images as shown in FIG. 3. On the left side of FIG. 3, there is an image obtained through triggering by prospective acquisition correction (PACE for short), and on the right side thereof, there is an image obtained through triggering by PT-Nav. The interference is from hardware and its root cause is complex, and it is therefore difficult to solve.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

Figure 1:
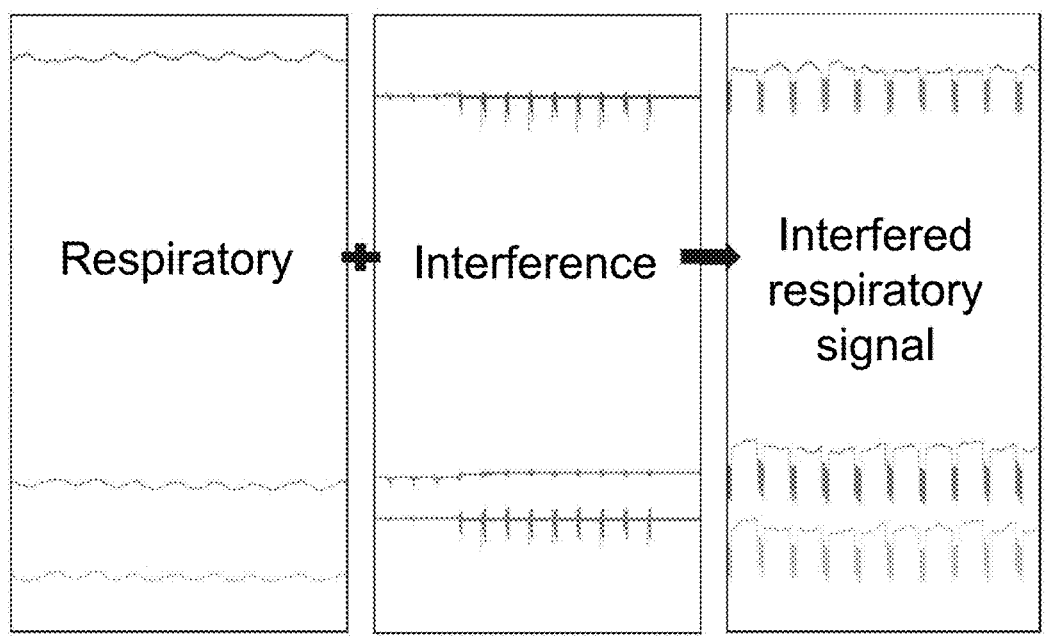
FIG. 1 is a schematic diagram of curves of signals in different channels.
Figure 2:
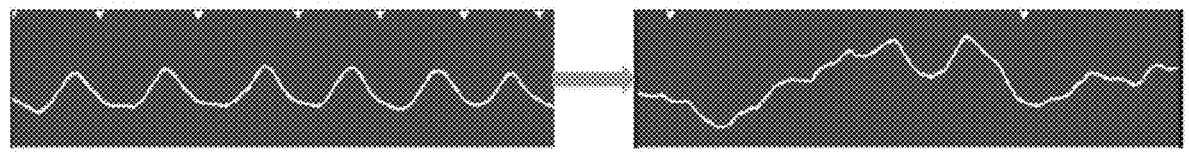
FIG. 2 is a curve of signals obtained after integrating signals in all channels.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure.

An object of the present disclosure is to provide a method for correcting the interference in respiratory navigation to at least solve the problem in the prior art that imaging quality is degraded due to interference in respiratory navigation signals.

In an exemplary embodiment of the present disclosure, a method for correcting the interference in respiratory navigation includes: transmitting, during magnetic resonance scanning, a respiratory signal generated by a radio frequency signal generator to a human body; acquiring, as a measured respiratory signal, a respiratory signal passing through the human body and acquired in a local coil, wherein the measured respiratory signal is constituted by a real respiratory signal and an interference signal; determining, according to a respiratory signal coil sensitivity of the real respiratory signal and an interference signal coil sensitivity of the interference signal, a signal relation that is satisfied by the real respiratory signal, the interference signal and the measured respiratory signal; and calculating the signal relation to obtain the real respiratory signal so as to correct the interference in the respiratory navigation. In an exemplary embodiment, the local coil has m channels, m is a natural number greater than 1, the respiratory signal coil sensitivity is a distribution ratio of the real respiratory signal in the m channels, and the interference signal coil sensitivity is a distribution ratio of the interference signal in the m channels.

Advantageously, in this way, the real respiratory signal is extracted from the actually acquired measured respiratory signal based on the respiratory signal coil sensitivity of the real respiratory signal and the interference signal coil sensitivity of the interference signal, so as to correct the interference in the respiratory navigation.

While magnetic resonance scanning is performed, that is, a pulse sequence is run, respiratory navigation is performed. Here, the respiratory navigation also uses the local coil as a respiratory signal receiver. Generally, the local coil has a plurality of channels according to a magnetic resonance system and protocol, and different channels represent different coil portions with different body parts covered. Therefore, respiratory signals acquired in the different channels are related to the position and geometric dimension of the coil, that is to say, sensitivities of the respiratory signals are different in the different channels and related to the position and geometric dimension of the coil. However, when a pulse sequence is run, an MR imaging signal may interfere with the respiratory signal, the sensitivity of the local coil to the interference signal is decided by the characteristics of a radio frequency component (i.e., decided by the magnetic resonance system itself), and the interference signal coil sensitivity can be calculated according to related knowledge. In principle, it can be considered that the respiratory signal and the interference are unrelated signals, and then the acquired signal is the sum of the two.

In an exemplary embodiment of the present disclosure, determining, according to a respiratory signal coil sensitivity of the real respiratory signal and an interference signal coil sensitivity of the interference signal, a signal relation that is satisfied by the real respiratory signal, the interference signal and the measured respiratory signal comprises: in the $n^{th}$ channel, the real respiratory signal Bre, the $n^{th}$ respiratory signal coil sensitivity an, the interference signal Dis, the $n^{th}$ interference signal coil sensitivity bn and the $n^{th}$ measured respiratory signal Signaln satisfy the $n^{th}$ signal relation:

$an*Bre+bn*Dis=$Signal$n$, and the signal relation satisfied in the entire local coil is:

$$\begin{bmatrix} a1 & b1 \\ a2 & b2 \\ \vdots & \vdots \\ am & bm \end{bmatrix} * \begin{bmatrix} Bre \\ Dis \end{bmatrix} = \begin{bmatrix} Signal1 \\ Signal2 \\ \vdots \\ Signalm \end{bmatrix},$$

where n is a natural number greater than 1 and less than or equal to m.

Since the respiratory signal coil sensitivity is the distribution ratio of the real respiratory signal in the channels, and the interference signal coil sensitivity is the distribution ratio of the interference signal in the channels, the component of the real respiratory signal that is received in the $n^{th}$ channel is equal to an*Bre, and correspondingly, the component of the interference signal that is received in the $n^{th}$ channel is equal to bn*Dis. As described above, if the respiratory signal and the interference are unrelated signals, the acquired signal is the sum of the two, that is, the measured respiratory signal Signaln=an*Bre+bn*Dis, and the relations in all channels:

$$a1*Bre + b1*Dis = Signal1$$
$$a2*Bre + b2*Dis = Signal2$$
$$\vdots$$
$$an*Bre + bn*Dis = Signaln$$

are integrated to obtain $$\begin{bmatrix} a1 & b1 \\ a2 & b2 \\ \vdots & \vdots \\ am & bm \end{bmatrix} * \begin{bmatrix} Bre \\ Dis \end{bmatrix} = \begin{bmatrix} Signal1 \\ Signal2 \\ \vdots \\ Signalm \end{bmatrix}.$$

In this way, the relationship satisfied by the real respiratory signal, the interference signal and the measured respiratory signal is quantitatively determined.

Further, according to an exemplary embodiment of the present disclosure, the calculating of the signal relation to obtain the real respiratory signal comprises: solving the signal relation, wherein when m is equal to 2, $$\begin{bmatrix} Bre \\ Dis \end{bmatrix} = \begin{bmatrix} a1 & b1 \\ a2 & b2 \\ \vdots & \vdots \\ am & bm \end{bmatrix}^{-1} * \begin{bmatrix} Signal1 \\ Signal2 \\ \vdots \\ Signalm \end{bmatrix};$$

and when m is greater than 2, $$\begin{bmatrix} Bre \\ Dis \end{bmatrix} = \begin{bmatrix} a1 & b1 \\ a2 & b2 \\ \vdots & \vdots \\ am & bm \end{bmatrix}^{+} * \begin{bmatrix} Signal1 \\ Signal2 \\ \vdots \\ Signalm \end{bmatrix},$$

wherein $$\begin{bmatrix} a1 & b1 \\ a2 & b2 \\ \vdots & \vdots \\ am & bm \end{bmatrix}^{+}$$

is the generalized inverse of $$\begin{bmatrix} a1 & b1 \\ a2 & b2 \\ \vdots & \vdots \\ am & bm \end{bmatrix},$$

and the first element in the vector $$\begin{bmatrix} Bre \\ Dis \end{bmatrix}$$

is extracted to obtain the real respiratory signal.

Here, the signal relation $$\begin{bmatrix} a1 & b1 \\ a2 & b2 \\ \vdots & \vdots \\ am & bm \end{bmatrix} * \begin{bmatrix} Bre \\ Dis \end{bmatrix} = \begin{bmatrix} Signal1 \\ Signal2 \\ \vdots \\ Signalm \end{bmatrix}$$

is a linear equation group, it is known from a related mathematical theory that when m is equal to 2, a coil sensitivity matrix is a square matrix $$\begin{bmatrix} a1 & b1 \\ a2 & b2 \end{bmatrix},$$

and in this case, me signal relation has a solution $$\begin{bmatrix} Bre \\ Dis \end{bmatrix} = \begin{bmatrix} a1 & b1 \\ a2 & b2 \end{bmatrix}^{-1} * \begin{bmatrix} Signal1 \\ Signal2 \end{bmatrix},$$

where $$\begin{bmatrix} a1 & b1 \\ a2 & b2 \end{bmatrix}^{-1}$$

is an inverse matrix of $$\begin{bmatrix} a1 & b1 \\ a2 & b2 \end{bmatrix}.$$

When m is greater than 2, the signal relation has a solution $$\begin{bmatrix} Bre \\ Dis \end{bmatrix} = \begin{bmatrix} a1 & b1 \\ a2 & b2 \\ \vdots & \vdots \\ am & bm \end{bmatrix}^{+} * \begin{bmatrix} Signal1 \\ Signal2 \\ \vdots \\ Signalm \end{bmatrix},$$

where $$\begin{bmatrix} a1 & b1 \\ a2 & b2 \\ \vdots & \vdots \\ am & bm \end{bmatrix}^{+}$$

is the Moore-Penrose generalized inverse of $$\begin{bmatrix} a1 & b1 \\ a2 & b2 \\ \vdots & \vdots \\ am & bm \end{bmatrix},$$

which can be subsequently obtained by means of full rank decomposition and singular value decomposition. In this way, the real respiratory signal can be calculated by using a well-established mathematical method.

In an exemplary embodiment of the present disclosure, the method further comprises pre-acquiring the measured respiratory signals for a predetermined time period as reference respiratory signals without magnetic resonance scanning.

In an exemplary embodiment, the pre-acquisition is performed without magnetic resonance scanning, that is, without running the pulse sequence, and in this case, the acquired signal does not contain the main interference generated by magnetic resonance signals. In this way, reference respiratory signals without interference are obtained.

Further, according to an embodiment of the present disclosure, the method further comprises: calculating a standard deviation of the reference respiratory signals as the respiratory signal coil sensitivity; and calculating an absolute signal strength of the reference respiratory signal as the interference signal coil sensitivity.

The standard deviation of the reference respiratory signals characterizes the degree of their fluctuations and thus the intensity level of respiratory motion, and thus can be used as the respiratory signal coil sensitivity. The absolute signal strength of the reference respiratory signals characterizes the amplitude values of the received signals, and although the received signals are respiratory signals, the ratio of the amplitude values in each channel is also applicable to the interference signal. In this way, the respiratory signal coil sensitivity and the interference signal coil sensitivity are quantitatively obtained.

In an exemplary embodiment of the present disclosure, the predetermined time period is greater than or equal to 3 seconds and less than or equal to 7 seconds.

In this way, sufficient signal samples can be acquired without affecting normal operating.

In an exemplary embodiment of the present disclosure, the respiratory signal generated by the radio frequency signal generator is a continuous wave radio frequency signal serving as a pilot tone signal.

The respiratory navigation here is pilot-triggered respiratory navigation, namely, PT-Nav. In this way, interference in the PT-Nav is corrected.

In an exemplary embodiment of the present disclosure, an apparatus for correcting the interference in respiratory navigation includes: a signal transmitter configured to transmit, during magnetic resonance scanning, a respiratory signal generated by a radio frequency signal generator to a human body; an acquisition module (acquirer) configured to acquire, as a measured respiratory signal, a respiratory signal passing through the human body and acquired in a local coil; a determination module (determiner) configured to determine, according to a respiratory signal coil sensitivity of the real respiratory signal and an interference signal coil sensitivity of the interference signal, a signal relation that is satisfied by the real respiratory signal, the interference signal and the measured respiratory signal; and a first calculator configured to calculate the signal relation to obtain the real respiratory signal so as to correct the interference in the respiratory navigation. In an exemplary embodiment, the measured respiratory signal comprises a real respiratory signal and an interference signal. In an exemplary embodiment, the local coil has a plurality of channels, the respiratory signal coil sensitivity is a distribution ratio of the real respiratory signal in the plurality of channels, and/or the interference signal coil sensitivity is a distribution ratio of the interference signal in the plurality of channels. In one or more aspects, the acquisition module and/or the pre-acquisition module are a signal receiver and/or a pre-receiver, respectively.

In an exemplary embodiment of the present disclosure, the apparatus further comprises: a pre-acquisition module (pre-acquirer) configured to pre-acquire the measured respiratory signals for a predetermined time period as reference respiratory signals without magnetic resonance scanning; and a second calculator configured to calculate a standard deviation of the reference respiratory signals as the respiratory signal coil sensitivity and calculate an absolute signal strength of the reference respiratory signals as the interference signal coil sensitivity. In an exemplary embodiment, the signal transmitter, pre-acquisition module, acquisition module, determination module, the first calculator, and/or the second calculator includes processor circuitry that is configured to perform one or more of the respective functions/operations of the signal transmitter, pre-acquisition module, acquisition module, determination module, the first calculator, and/or the second calculator.

Here, the foregoing explanation and advantages of the method according to the present disclosure are also applicable to the corresponding apparatus according to the present disclosure.

In an aspect of the present disclosure, a storage medium is further provided, which comprises a stored program, wherein when the program is run, a device on which the storage medium is located is controlled to perform the method according to the present disclosure.

In an embodiment of the present disclosure, a method for correcting the interference in respiratory navigation includes calculating the real respiratory signal according to the signal relation determined by the respiratory signal coil sensitivity and the interference signal coil sensitivity. Advantageously, the method solves the problem in the prior art where imaging quality is degraded due to interference in respiratory navigation signals, thereby achieving the technical effects of improving the imaging quality of the magnetic resonance system.

Figure 4:
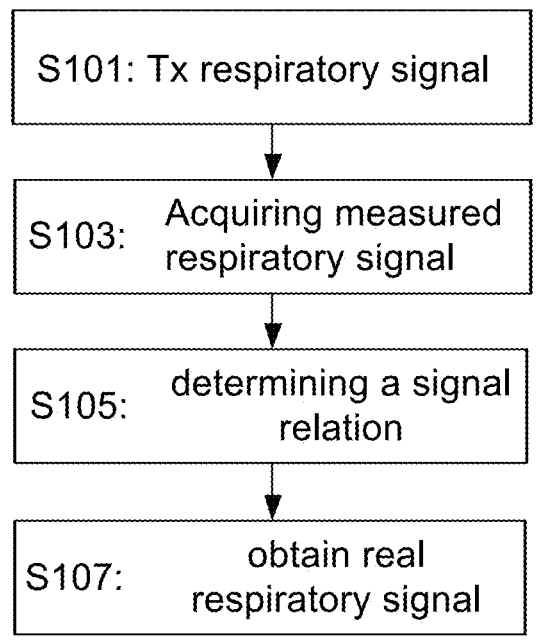
FIG. 4 is a flowchart of a method for correcting the interference in respiratory navigation according to an exemplary embodiment of the present disclosure.

FIG. 4 illustrates a flowchart of a method for correcting the interference in respiratory navigation according to an exemplary embodiment. As shown in FIG. 4, the method for correcting the interference in respiratory navigation includes: in step S101, transmitting, during magnetic resonance scanning, a respiratory signal generated by a radio frequency signal generator to a human body; in step S103, acquiring, as a measured respiratory signal, a respiratory signal passing through the human body and acquired in a local coil, wherein the measured respiratory signal is constituted by a real respiratory signal and an interference signal; in step S105, determining, according to a respiratory signal coil sensitivity of the real respiratory signal and an interference signal coil sensitivity of the interference signal, a signal relation that is satisfied by the real respiratory signal, the interference signal and the measured respiratory signal; and in step S107, calculating the signal relation to obtain the real respiratory signal so as to correct the interference in the respiratory navigation, wherein the local coil has m channels, m is a natural number greater than 1, the respiratory signal coil sensitivity is a distribution ratio of the real respiratory signal in the m channels, and the interference signal coil sensitivity is a distribution ratio of the interference signal in the m channels.

In this way, the real respiratory signal is extracted from the actually acquired measured respiratory signal based on the respiratory signal coil sensitivity of the real respiratory signal and the interference signal coil sensitivity of the interference signal, so as to correct the interference in the respiratory navigation.

In an exemplary embodiment, the determining, according to a respiratory signal coil sensitivity of the real respiratory signal and an interference signal coil sensitivity of the interference signal, of a signal relation that is satisfied by the real respiratory signal, the interference signal and the measured respiratory signal comprises: in the $n^{th}$ channel, the real respiratory signal Bre, the $n^{th}$ respiratory signal coil sensitivity an, the interference signal Dis, the $n^{th}$ interference signal coil sensitivity bn and the $n^{th}$ measured respiratory signal Signaln satisfy the $n^{th}$ signal relation:

$$an*Bre+bn*Dis=\text{Signal}n,$$

and the signal relation satisfied in the entire local coil is:

$$\begin{bmatrix} a1 & b1 \\ a2 & b2 \\ \vdots & \vdots \\ am & bm \end{bmatrix} * \begin{bmatrix} Bre \\ Dis \end{bmatrix} = \begin{bmatrix} Signal1 \\ Signal2 \\ \vdots \\ Signalm \end{bmatrix},$$

where n is a natural number greater than 1 and less than or equal to m.

Since the respiratory signal coil sensitivity is the distribution ratio of the real respiratory signal in the channels, and the interference signal coil sensitivity is the distribution ratio of the interference signal in the channels, the component of the real respiratory signal that is received in the $n^{th}$ channel is equal to an*Bre, and correspondingly, the component of the interference signal that is received in the $n^{th}$ channel is equal to bn*Dis. As described above, if the respiratory signal and the interference are unrelated signals, the acquired signal is the sum of the two, that is, the measured respiratory signal Signaln=an*Bre+bn*Dis, and the relations in all channels:

$$a1*Bre+b1*Dis = Signal1$$
$$a2*Bre+b2*Dis = Signal2$$
$$\vdots$$
$$an*Bre+bn*Dis = Signaln$$

are integrated to obtain $$\begin{bmatrix} a1 & b1 \\ a2 & b2 \\ \vdots & \vdots \\ am & bm \end{bmatrix} * \begin{bmatrix} Bre \\ Dis \end{bmatrix} = \begin{bmatrix} Signal1 \\ Signal2 \\ \vdots \\ Signalm \end{bmatrix}.$$

In this way, the relationship satisfied by the real respiratory signal, the interference signal and the measured respiratory signal is quantitatively determined.

In an exemplary embodiment, the calculating of the signal relation to obtain the real respiratory signal comprises: solving the signal relation, wherein when m is equal to 2, $$\begin{bmatrix} Bre \\ Dis \end{bmatrix} = \begin{bmatrix} a1 & b1 \\ a2 & b2 \\ \vdots & \vdots \\ am & bm \end{bmatrix}^{-1} * \begin{bmatrix} Signal1 \\ Signal2 \\ \vdots \\ Signalm \end{bmatrix};$$

and when m is greater than 2, $$\begin{bmatrix} Bre \\ Dis \end{bmatrix} = \begin{bmatrix} a1 & b1 \\ a2 & b2 \\ \vdots & \vdots \\ am & bm \end{bmatrix}^{+} * \begin{bmatrix} Signal1 \\ Signal2 \\ \vdots \\ Signalm \end{bmatrix},$$

wherein $$\begin{bmatrix} a1 & b1 \\ a2 & b2 \\ \vdots & \vdots \\ am & bm \end{bmatrix},$$

is the generalized inverse of $$\begin{bmatrix} a1 & b1 \\ a2 & b2 \\ \vdots & \vdots \\ am & bm \end{bmatrix}^+$$

and the first element in the vector $$\begin{bmatrix} Bre \\ Dis \end{bmatrix}$$

is extracted to obtain the real respiratory signal.

Here, the signal relation $$\begin{bmatrix} a1 & b1 \\ a2 & b2 \\ \vdots & \vdots \\ am & bm \end{bmatrix} * \begin{bmatrix} Bre \\ Dis \end{bmatrix} = \begin{bmatrix} Signal1 \\ Signal2 \\ \vdots \\ Signalm \end{bmatrix}$$

is a linear equation group, it is known from a related mathematical theory that when m is equal to 2, a coil sensitivity matrix is a square matrix $$\begin{bmatrix} a1 & b1 \\ a2 & b2 \end{bmatrix},$$

and in this case, me signal relation has a solution $$\begin{bmatrix} Bre \\ Dis \end{bmatrix} = \begin{bmatrix} a1 & b1 \\ a2 & b2 \end{bmatrix}^{-1} * \begin{bmatrix} Signal1 \\ Signal2 \end{bmatrix},$$

where $$\begin{bmatrix} a1 & b1 \\ a2 & b2 \end{bmatrix}^{-1}$$

is an inverse matrix of $$\begin{bmatrix} a1 & b1 \\ a2 & b2 \end{bmatrix}.$$

When m is greater than 2, the signal relation has a solution $$\begin{bmatrix} Bre \\ Dis \end{bmatrix} = \begin{bmatrix} a1 & b1 \\ a2 & b2 \\ \vdots & \vdots \\ am & bm \end{bmatrix}^+ * \begin{bmatrix} Signal1 \\ Signal2 \\ \vdots \\ Signalm \end{bmatrix},$$

where $$\begin{bmatrix} a1 & b1 \\ a2 & b2 \\ \vdots & \vdots \\ am & bm \end{bmatrix}^+$$

is the Moore-Penrose generalized inverse of $$\begin{bmatrix} a1 & b1 \\ a2 & b2 \\ \vdots & \vdots \\ am & bm \end{bmatrix},$$

which can be subsequently obtained by means of full rank decomposition and singular value decomposition. In this way, the real respiratory signal can be calculated by using a well-established mathematical method.

In an exemplary embodiment, the method further comprises pre-acquiring the measured respiratory signals for a predetermined time period as reference respiratory signals without magnetic resonance scanning.

In an exemplary embodiment, the method further comprises: calculating a standard deviation of the reference respiratory signals as the respiratory signal coil sensitivity; and calculating an absolute signal strength of the reference respiratory signal as the interference signal coil sensitivity.

In an exemplary embodiment, the predetermined time period is greater than or equal to 3 seconds and less than or equal to 7 seconds.

In this way, sufficient signal samples can be acquired without affecting normal operating.

In an exemplary embodiment, the respiratory signal generated by the radio frequency signal generator is a continuous wave radio frequency signal serving as a pilot tone signal.

The respiratory navigation here is pilot tone-triggered respiratory navigation, namely, PT-Nav. In this way, the interference in the PT-Nav is corrected.

Figure 5:
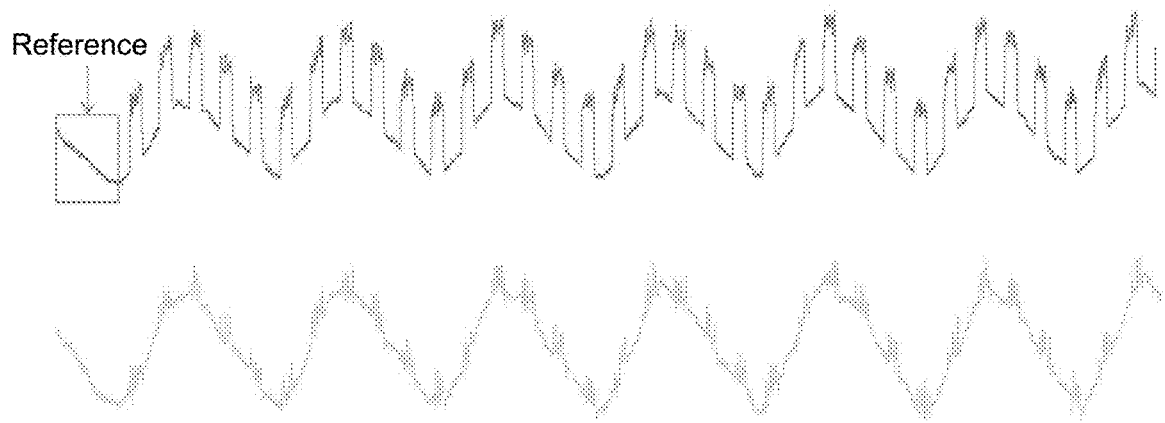
FIG. 5 shows a diagram of signals acquired during pre-acquisition and a diagram of corrected signals in a method for correcting the interference in respiratory navigation according to an exemplary embodiment of the present disclosure.

FIG. 5 shows a diagram of signals acquired during pre-acquisition and a diagram of corrected signals in a method for correcting the interference in respiratory navigation according to an exemplary embodiment of the present disclosure. The curve of signals in the upper part of FIG. 5 represents actual measured respiratory signals to which pre-acquisition is applied. It can be seen that the signals acquired at the beginning of the pre-acquisition phase do not contain interference, and the signals acquired subsequently have already contained real respiratory signals and interference signals. The curve of signals in the lower part of FIG. 5 is a curve of corrected signals that undergo the method according to the present disclosure, and it can be seen that many "signal drops" caused by interference signals have been removed in this case.

Figure 3:
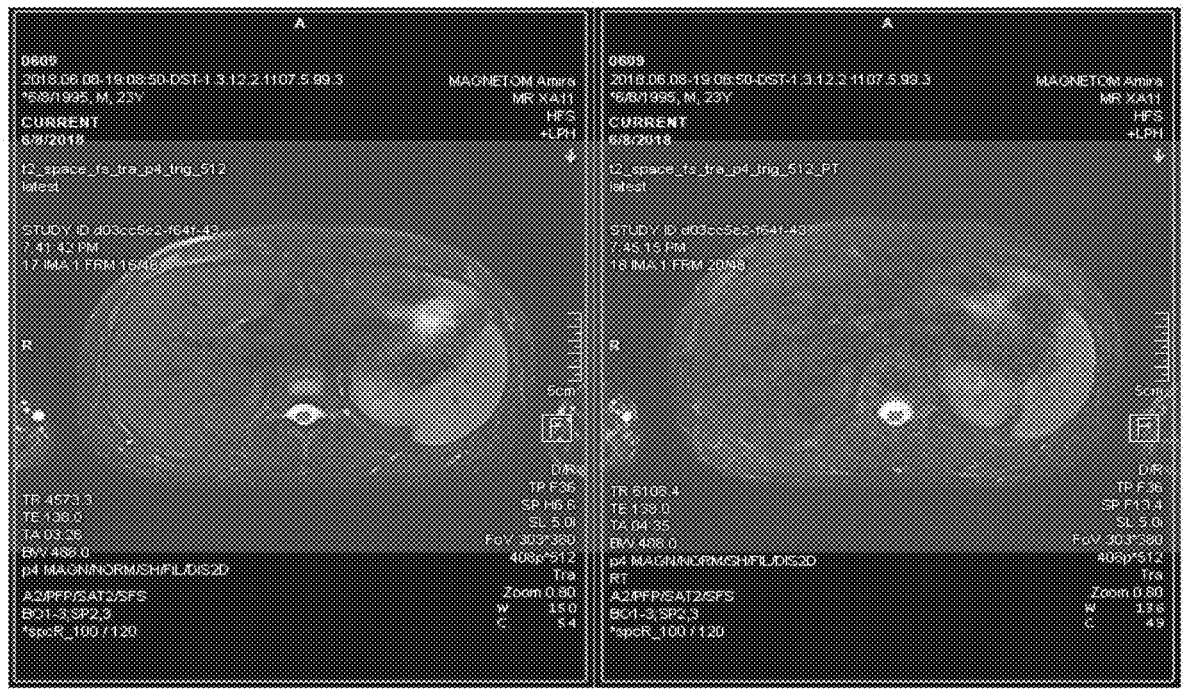
FIG. 3 is a comparison of conventional MRI images.
Figure 6:
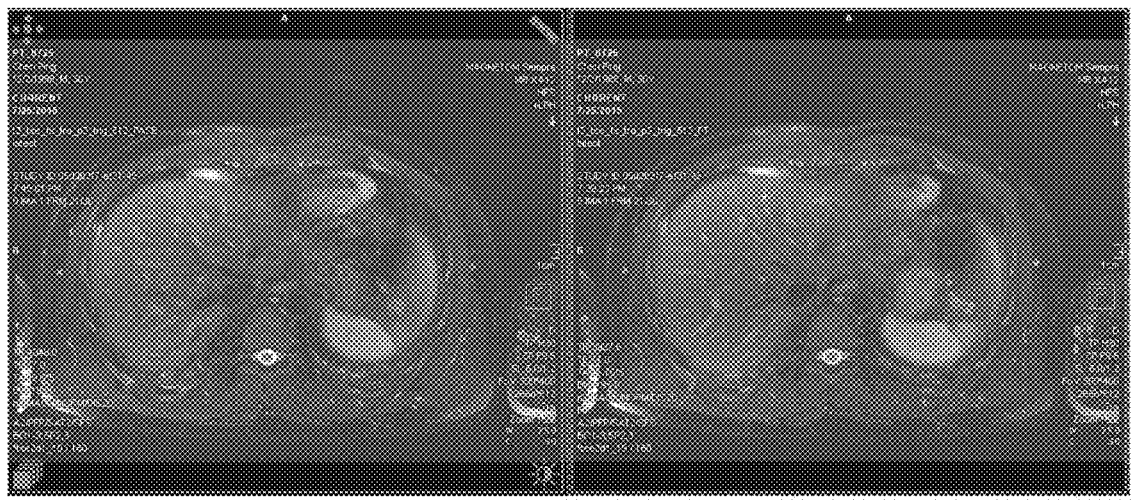
FIG. 6 is a comparison of MRI images obtained using the method according to the present disclosure, which corresponds to FIG. 3.

FIG. 6 shows a comparison of MRI images obtained using the method according to the present disclosure, which corresponds to FIG. 3. On the left side, there is an image obtained through triggering by PACE, and on the right side, there is an image obtained through triggering by PT-Nav after interference correction according to the present disclosure is used. It can be seen that the imaging quality is significantly improved.

Figure 7:
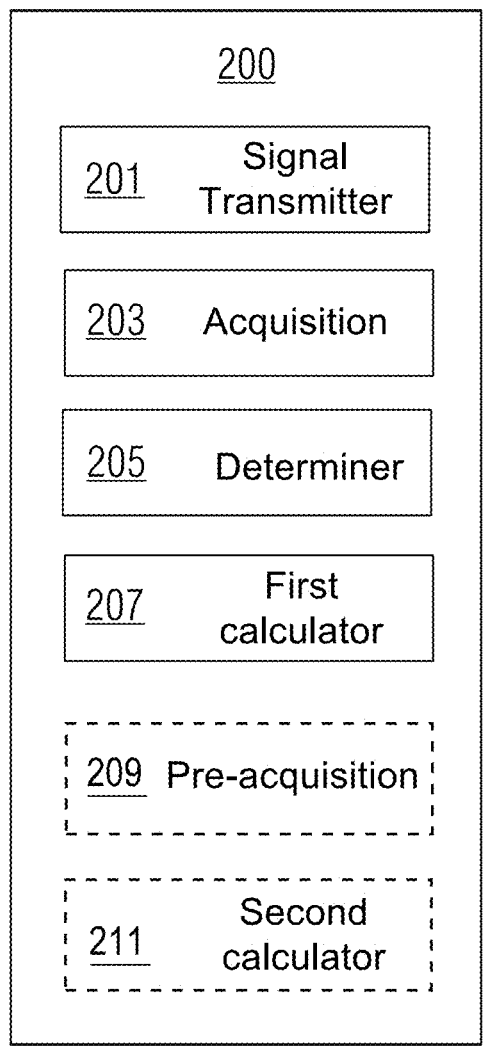
FIG. 7 is a schematic diagram of an apparatus for correcting the interference in respiratory navigation according to an exemplary embodiment of the present disclosure.

FIG. 7 illustrates an apparatus 200 for correcting the interference in respiratory navigation according to an exemplary embodiment. As shown in FIG. 7, the apparatus for correcting the interference comprises: a signal transmitter 201 configured to transmit, during magnetic resonance scanning, a respiratory signal generated by a radio frequency signal generator to a human body; an acquisition module (acquirer) 203 configured to acquire, as a measured respiratory signal, a respiratory signal passing through the human body and acquired in a local coil; a determination module (determiner) 205 configured to determine, according to a respiratory signal coil sensitivity of the real respiratory signal and an interference signal coil sensitivity of the interference signal, a signal relation that is satisfied by the real respiratory signal, the interference signal and the measured respiratory signal; and a first calculator 207 configured to calculate the signal relation to obtain the real respiratory signal so as to correct the interference in the respiratory navigation. In an exemplary embodiment, the measured respiratory signal is constituted by a real respiratory signal and an interference signal. In an exemplary embodiment, the local coil has a plurality of channels, the respiratory signal coil sensitivity is a distribution ratio of the real respiratory signal in the plurality of channels, and the interference signal coil sensitivity is a distribution ratio of the interference signal in the plurality of channels.

In an exemplary embodiment, the apparatus for correcting the interference further comprises: a pre-acquisition module (pre-acquirer) 209 configured to pre-acquire the measured respiratory signals for a predetermined time period as reference respiratory signals without magnetic resonance scanning; and a second calculator 211 configured to calculate a standard deviation of the reference respiratory signals as the respiratory signal coil sensitivity and calculate an absolute signal strength of the reference respiratory signals as the interference signal coil sensitivity.

According to another aspect of an embodiment of the present disclosure, a storage medium is further provided, which comprises a stored program, wherein when the program is run, a device on which the storage medium is located is controlled to perform the method according to the present disclosure.

In an exemplary embodiment, the apparatus 200 (including one or more of the components of the apparatus 200: the signal transmitter, pre-acquisition module, acquisition module, determination module, the first calculator, and/or the second calculator) includes processor circuitry that is configured to perform one or more functions/operations of the apparatus 200 (including one or more of the respective functions of the signal transmitter, pre-acquisition module, acquisition module, determination module, the first calculator, and/or the second calculator.

In a method for correcting the interference in respiratory navigation according to an exemplary embodiment, the real respiratory signal is calculated according to the signal relation determined by the respiratory signal coil sensitivity and the interference signal coil sensitivity. Advantageously, the method according to the present disclosure solves the problem in the prior art that imaging quality is degraded due to interference in respiratory navigation signals, thereby achieving the technical effect of improving the imaging quality of the magnetic resonance system.

In the above embodiments of the present disclosure, the various embodiments have been described with different emphases, and the portions that are not detailed in a certain embodiment may be considered with respect to the related descriptions of other embodiments.

In several embodiments provided in the present disclosure, it should be understood that the disclosed technical content may be implemented in other manners. The apparatus embodiments described above are merely schematic. For example, the division of the units or modules is only a logical function division, and in actual implementations, there may be another division manner. For example, a plurality of units or modules or components may be combined or integrated into another system, or some features may be omitted or not implemented. In addition, the mutual coupling or direct coupling or communication connection shown or discussed may be an indirect coupling or communication connection through some interfaces, modules or units, and may be electrical or otherwise.

The units or modules described as separate components may or may not be physically separated, and the components displayed as units or modules may or may not be physical units or modules, that is, the components may be located in one place, or may be distributed on a plurality of network units or modules. Some or all of the units or modules may be selected according to actual needs to achieve the objective of the solution of the embodiment.

In addition, each functional unit or module in various embodiments of the present disclosure may be integrated into one processing unit or module, or each unit or module may be physically present separately, or two or more units or modules may be integrated into one unit or module. The above integrated unit or module can be implemented in the form of hardware or in the form of a software functional unit or module.

The integrated unit, if implemented in the form of a software functional unit and sold or used as an independent product, may be stored in a computer readable storage medium. Based on such understanding, the technical solution of the present disclosure, in essence or the contribution to the prior art, or all or part of the technical solution may be embodied in the form of a software product. The computer software product is stored in a storage medium, and includes a plurality of instructions used to cause a computer device (which may be a personal computer, a server, or a network device, etc.) to perform all or part of the steps of the method described in various embodiments of the present disclosure. Moreover, the aforementioned storage medium comprises: a variety of media that can store program code, such as a USB flash disk, a read-only memory (ROM), a random access memory (RAM), a mobile hard disk, a magnetic disk, or an optical disc.

It needs to be noted that the terms such as "first" and "second" in the description and claims of the present disclosure as well as the accompanying drawings are used to distinguish similar objects, and are not necessarily used to describe a specific order of precedence. It is to be understood that the data used in this way may be interchanged where appropriate, so that the embodiments of the present disclosure described herein can be implemented in a sequence other than those illustrated or described herein. In addition, the terms "include" and "have" and any variations thereof are intended to cover non-exclusive inclusions. For example, a process, method, system, product, or device that includes a series of steps, modules, or units is not necessarily limited to those steps, modules, or units that are explicitly listed, but may include other steps, modules, or units not explicitly listed or inherent to such processes, methods, products, or devices.

The above descriptions are only preferred embodiments of the present disclosure, and it should be noted that those of ordinary skill in the art can also make several improvements and modifications without departing from the principle of the present disclosure, and these improvements and modifications should also be considered to be within the scope of protection of the present disclosure.

Any connection or coupling between functional blocks, devices, components of physical or functional units shown in the drawings and described hereinafter may be implemented by an indirect connection or coupling. A coupling between components may be established over a wired or wireless connection. Functional blocks may be implemented in hardware, software, firmware, or a combination thereof.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general purpose computer.

For the purposes of this discussion, the term "processor circuitry" shall be understood to be circuit(s), processor(s), logic, or a combination thereof. A circuit includes an analog circuit, a digital circuit, state machine logic, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. A method for correcting interference in a respiratory navigation, comprising:
transmitting, during magnetic resonance scanning, a respiratory signal, generated by a radio frequency signal generator, to a human body;
acquiring, as a measured respiratory signal, a respiratory signal passing through the human body and acquired in a local coil, wherein the measured respiratory signal includes a real respiratory signal and an interference signal;
determining, based on a respiratory signal coil sensitivity of the real respiratory signal and an interference signal coil sensitivity of the interference signal, a signal relation that is satisfied by the real respiratory signal, the interference signal, and the measured respiratory signal; and
calculating the signal relation to obtain the real respiratory signal so as to correct the interference in the respiratory navigation, wherein:
the local coil has m channels, m being a natural number greater than 1,
the respiratory signal coil sensitivity is a distribution ratio of the real respiratory signal in the m channels, and
the interference signal coil sensitivity is a distribution ratio of the interference signal in the m channels.

2. The method as claimed in claim 1, wherein the determining of the signal relation that is satisfied by the real respiratory signal, the interference signal, and the measured respiratory signal comprises:
in the $n^{th}$ channel, the real respiratory signal Bre, the $n^{th}$ respiratory signal coil sensitivity an, the interference signal Dis, the $n^{th}$ interference signal coil sensitivity bn and the $n^{th}$ measured respiratory signal Signaln satisfy the $n^{th}$ signal relation:

$$an*Bre+bn*Dis=Signaln,$$

and the signal relation satisfied in an entirety of the local coil is:

$$\begin{bmatrix} a1 & b1 \\ a2 & b2 \\ \vdots & \vdots \\ am & bm \end{bmatrix} * \begin{bmatrix} Bre \\ Dis \end{bmatrix} = \begin{bmatrix} Signal1 \\ Signal2 \\ \vdots \\ Signalm \end{bmatrix},$$

where n is a natural number greater than 1 and less than or equal to m.

3. The method as claimed in claim 2, wherein the calculating of the signal relation to obtain the real respiratory signal comprises solving the signal relation, wherein:
when m is equal to 2, $$\begin{bmatrix} Bre \\ Dis \end{bmatrix} = \begin{bmatrix} a1 & b1 \\ a2 & b2 \\ \vdots & \vdots \\ am & bm \end{bmatrix}^{-1} * \begin{bmatrix} Signal1 \\ Signal2 \\ \vdots \\ Signalm \end{bmatrix};$$

and
when m is greater than 2:

$$\begin{bmatrix} Bre \\ Dis \end{bmatrix} = \begin{bmatrix} a1 & b1 \\ a2 & b2 \\ \vdots & \vdots \\ am & bm \end{bmatrix}^{+} * \begin{bmatrix} Signal1 \\ Signal2 \\ \vdots \\ Signalm \end{bmatrix},$$

wherein $$\begin{bmatrix} a1 & b1 \\ a2 & b2 \\ \vdots & \vdots \\ am & bm \end{bmatrix}^{+}$$

is the generalized inverse of $$\begin{bmatrix} a1 & b1 \\ a2 & b2 \\ \vdots & \vdots \\ am & bm \end{bmatrix},$$

and
the first element in the vector $$\begin{bmatrix} Bre \\ Dis \end{bmatrix}$$

is extracted to obtain the real respiratory signal.

4. The method as claimed in claim 1, wherein further comprising pre-acquiring measured respiratory signals for a predetermined time period as reference respiratory signals without magnetic resonance scanning.

5. The method as claimed in claim 4, further comprising:
calculating a standard deviation of the reference respiratory signals as the respiratory signal coil sensitivity; and
calculating an absolute signal strength of the reference respiratory signals as the interference signal coil sensitivity.

6. The method as claimed in claim 4, wherein the predetermined time period is greater than or equal to 3 seconds and less than or equal to 7 seconds.

7. The method as claimed in claim 4, further comprising calculating a standard deviation of the reference respiratory signals as the respiratory signal coil sensitivity.

8. The method as claimed in claim 4, further comprising calculating an absolute signal strength of the reference respiratory signals as the interference signal coil sensitivity.

9. The method as claimed in claim 1, wherein the respiratory signal generated by the radio frequency signal generator is a continuous wave radio frequency signal serving as a pilot signal.

10. A non-transitory computer-readable storage medium with an executable program stored thereon, that when executed, instructs a processor to perform the method of claim 1.

11. A computer program product having a computer program which is directly loadable into a memory of a medical imaging system, when executed by a processor of the medical imaging system, causes the processor to perform the method as claimed in claim 1.

12. The method as claimed in claim 1, wherein transmitting the respiratory signal during the magnetic resonance scanning comprises transmitting the respiratory signal during an imaging pulse sequence of the magnetic resonance scanning.

13. An apparatus for correcting interference in a respiratory navigation, comprising:
a signal transmitter configured to transmit, during magnetic resonance scanning, a respiratory signal, generated by a radio frequency signal generator, to a human body;
an acquisition module configured to acquire, as a measured respiratory signal, a respiratory signal passing through the human body and acquired in a local coil, the measured respiratory signal including a real respiratory signal and an interference signal;
a determination module configured to determine, based on a respiratory signal coil sensitivity of the real respiratory signal and an interference signal coil sensitivity of the interference signal, a signal relation that is satisfied by the real respiratory signal, the interference signal, and the measured respiratory signal; and
a first calculator configured to calculate the signal relation to obtain the real respiratory signal so as to correct the interference in the respiratory navigation, wherein:
the local coil has a plurality of channels,
the respiratory signal coil sensitivity is a distribution ratio of the real respiratory signal in the plurality of channels, and
the interference signal coil sensitivity is a distribution ratio of the interference signal in the plurality of channels.

14. The apparatus as claimed in claim 13, further comprising:
a pre-acquisition module configured to pre-acquire measured respiratory signals for a predetermined time period as reference respiratory signals without magnetic resonance scanning; and
a second calculator configured to calculate a standard deviation of the reference respiratory signals as the respiratory signal coil sensitivity and calculate an absolute signal strength of the reference respiratory signals as the interference signal coil sensitivity.

15. The apparatus as claimed in claim 13, wherein the respiratory signal generated by the radio frequency signal generator is a continuous wave radio frequency signal serving as a pilot signal.

16. An apparatus for correcting interference in a respiratory navigation, comprising:
a memory; and a processor configured to execute computer instructions stored in the memory to cause the processor to:
  transmit, during magnetic resonance scanning, a respiratory signal, generated by a radio frequency signal generator, to a human body;
  acquire, as a measured respiratory signal, a respiratory signal passing through the human body and acquired in a local coil, the measured respiratory signal including a real respiratory signal and an interference signal;
  determine, based on a respiratory signal coil sensitivity of the real respiratory signal and an interference signal coil sensitivity of the interference signal, a signal relation that is satisfied by the real respiratory signal, the interference signal, and the measured respiratory signal; and
  calculate the signal relation to obtain the real respiratory signal so as to correct the interference in the respiratory navigation, wherein:
the local coil has a plurality of channels,
  the respiratory signal coil sensitivity is a distribution ratio of the real respiratory signal in the plurality of channels, and
  the interference signal coil sensitivity is a distribution ratio of the interference signal in the plurality of channels.

17. The apparatus as claimed in claim 16, wherein the processor is further configured to:
  pre-acquire measured respiratory signals for a predetermined time period as reference respiratory signals without magnetic resonance scanning; and
  calculate a standard deviation of the reference respiratory signals as the respiratory signal coil sensitivity and calculate an absolute signal strength of the reference respiratory signals as the interference signal coil sensitivity.

18. The apparatus as claimed in claim 16, wherein the respiratory signal generated by the radio frequency signal generator is a continuous wave radio frequency signal serving as a pilot signal.

* * * * *